United States Patent [19]

Matsumoto et al.

[11] Patent Number: 4,877,804
[45] Date of Patent: Oct. 31, 1989

[54] THIADIAZOLE DERIVATIVE, AND INSECTICIDAL AND MITICIDAL COMPOSITION CONTAINING THE DERIVATIVE AS THE EFFECTIVE INGREDIENT

[75] Inventors: Susumu Matsumoto, Yokohama; Hiroki Ohta, Kokubunji; Masahiro Yamada, Machida; Yoshiaki Higashino; Toshiki Fukuchi, both of Yokohama, all of Japan

[73] Assignee: Mitsubishi Chemical Industries Limited, Tokyo, Japan

[21] Appl. No.: 176,297

[22] Filed: Mar. 31, 1988

[30] Foreign Application Priority Data

Mar. 31, 1987 [JP] Japan .................. 62-78311

[51] Int. Cl.$^4$ .................. C07D 417/10; A61K 31/44
[52] U.S. Cl. .................. 514/342; 546/277
[58] Field of Search .................. 546/277; 514/342

[56] References Cited

U.S. PATENT DOCUMENTS 4,141,984 2/1979 Ward .
4,271,166 6/1981 Ward .

FOREIGN PATENT DOCUMENTS 0092706 of 0000 European Pat. Off. .
0239047 9/1987 European Pat. Off. .
105173 of 1977 Japan .
48768 of 1979 Japan .
215675 of 1985 Japan .

Primary Examiner—Jane T. Fan
Attorney, Agent, or Firm—Oblon, Spivak, McClelland, Maier & Neustadt

[57] ABSTRACT

A thiadiazole derivative represented by the formula (I):

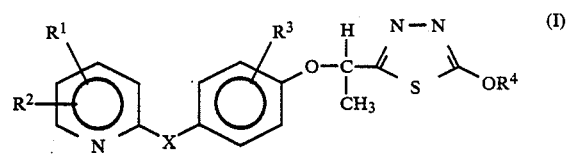

wherein $R^1$ and $R^2$ independently represent hydrogen atom, halogen atom, lower haloalkyl group, lower alkoxycarbonyl group or cyano group, $R^3$ represents hydrogen atom or halogen atom, $R^4$ represents lower alkyl group, X represents oxygen atom or sulfur atom, as well as an insecticidal and miticidal composition containing the derivative as the effective ingredient are disclosed.

The thiadiazole derivative according to the present invention has excellent controlling effect even against harmful insects and mites showing resistance to conventional insecticide.

9 Claims, No Drawings

THIADIAZOLE DERIVATIVE, AND INSECTICIDAL AND MITICIDAL COMPOSITION CONTAINING THE DERIVATIVE AS THE EFFECTIVE INGREDIENT

BACKGROUND OF THE INVENTION

The present invention relates to a novel thiadiazole derivative, and an insecticidal and miticidal composition containing the derivative as the effective ingredient.

Organic phosphorous compounds, organic chlorine compounds, etc. have been used as agricultural and horticultural insecticides and miticides, but, during use of such chemicals for long times, harmful insects and mites have aquired resistance to conventional insecticides and miticides and their control has become difficult. While on the other hand, N-thiadiazolylbenzamide derivatives having thiadiazole rings are disclosed as the heterocyclic compounds having insecticidal activity in Japanese Patent Laying-Open (KOKAI) Nos. 52-105173 and 54-48768.

In addition, some of organic phosphorous compounds or organic chlorine compounds exhibit high toxicity and others are highly residual to disturb the ecosystem and bring about extremely anxious states. Accordingly, it has been expected for the development of a novel compound showing excellent controlling effect against harmful insects and mites having aquired resistance to conventional pesticides and miticides, showing low toxicity and being less residual, as well as insecticidal and miticidal composition containing such a compound as the effective ingredient.

The present inventors have made an earnest study to dissolve the foregoing problems and, as a result, have accomplished the present invention based on the finding of a novel thiadiazole derivative having a chemical structure quite different from that in organic phosphorous compounds, organic chlorine compounds and N-thiadiazolylbenzamide derivatives as conventional insecticidal and miticidal composition, and showing controlling effect against harmful insects and mites having aquired resistance to conventional pesticides.

SUMMARY OF THE INVENTION

In a first aspect of the present invention, there is provided a thiadiazole derivative represented by the formula (I):

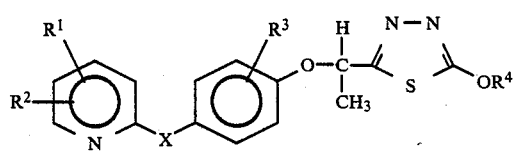

wherein $R^1$ and $R^2$ independently represent hydrogen atom, halogen atom, lower haloalkyl group, lower alkoxycarbonyl group or cyano group, $R^3$ represents hydrogen atom or halogen atom, $R^4$ represents lower alkyl group, X represents oxygen atom or sulfur atom.

In a second aspect of the present invention, there is provided an insecticidal and miticidal composition comprising, as the effective ingredient, an insecticidally and miticidally effective amount of a thiadiazole derivative represented by the formula (I):

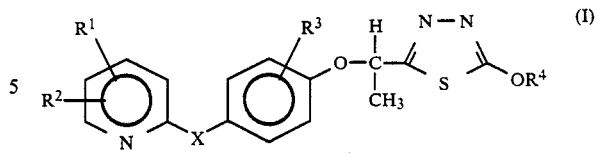

wherein $R^1$ and $R^2$ independently represent hydrogen atom, halogen atom, lower haloalkyl group, lower alkoxycarbonyl group or cyano group, $R^3$ represents hydrogen atom or halogen atom, $R^4$ represents lower alkyl group, X represents oxygen atom or sulfur atom, and insecticidally and miticidally acceptable adjuvant(s).

In a third aspect of the present invention, there is provided a process for producing a thiadiazole derivative represented by the formula (I):

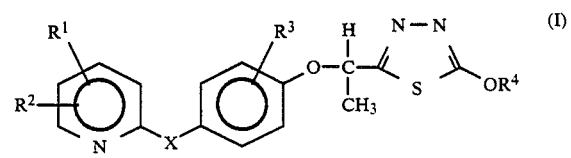

wherein $R^1$ and $R^2$ independently represent hydrogen atom, halogen atom, lower haloalkyl group, lower alkoxycarbonyl group or cyano group, $R^3$ represents hydrogen atom or halogen atom, $R^4$ represents lower alkyl group, X represents oxygen atom or sulfur atom, which comprises reacting a phenol derivative represented by the formula (II):

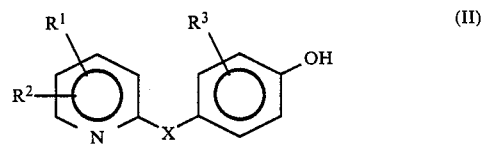

wherein $R^1$, $R^2$, $R^3$ and X have the same meanings as defined above, with a thiadiazole derivative represented by the formula (III):

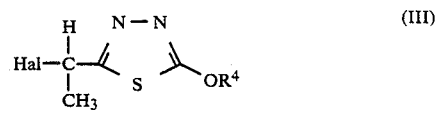

wherein $R^4$ represents the same meaning as defined above and Hal represents halogen atom, in the presence of a base.

In a fourth aspect of the present invention, there is provided a process for producing a thiadiazole derivative represented by the formula (I):

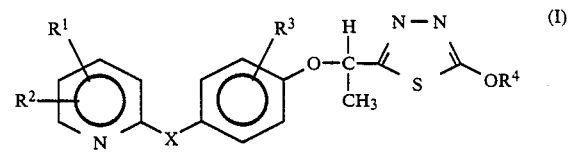

wherein $R^1$ and $R^2$ independently represent hydrogen atom, halogen atom, lower haloalkyl group, lower alkoxycarbonyl group or cyano group, $R^3$ represents hydrogen atom or halogen atom, $R^4$ represents lower alkyl group, X represents oxygen atom or sulfur atom, which comprises cyclizing a hydrazine derivative represented by the formula (IV):

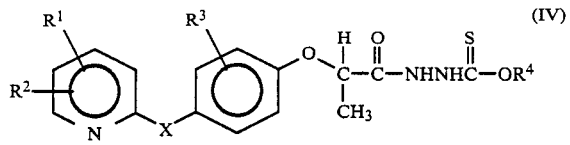

(IV)

wherein $R^1$, $R^2$, $R^3$, $R^4$ and X have the same meanings as defined above, under the presence of a dehydrating agent.

DETAILED DESCRIPTION OF THE INVENTION

The present invention relates to a novel thiadiazole derivative represented by the formula (I) and an insecticidal and miticidal composition containing the derivative as the effective ingredient.

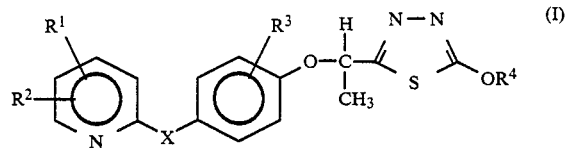

(I)

In the formula (I), $R^1$ and $R^2$ independently represent hydrogen atom, halogen atom, lower haloalkyl group, lower alkoxycarbonyl group or cyano group. Preferred halogen atom is fluorine atom, chlorine atom or bromine atom. Preferred lower haloalkyl group is a $C_1$-$C_4$ alkyl group which is substituted with from 1 to 9 halogen atoms, preferably, fluorine atoms, chlorine atoms or bromine atoms. More preferred lower haloalkyl group is a $C_1$-$C_2$ alkyl group which is substituted with from 1 to 5, preferably 2 to 5 halogen atoms, preferably, fluorine atoms, chlorine atoms or bromine atoms. A preferred lower alkoxycarbonyl group is an alkoxycarbonyl group having 2 to 5, preferably, 2 carbon atoms. Among these variables for $R^1$ and $R^2$, hydrogen atom, halogen atom, trifluoromethyl group and cyano group are particularly preferred.

$R^3$ represents hydrogen atom or halogen atom such as fluorine atom, chlorine atom and bromine atom. $R^4$ represents lower alkyl group, preferably, $C_1$-$C_4$ alkyl group and particularly preferably, $C_1$-$C_3$ alkyl group. X represents oxygen atom or sulfur atom, the oxygen atom being particularly preferred.

The thiadiazole derivative of the present invention represented by the formula (I) can be produced by reacting a phenol derivative represented by the formula (II):

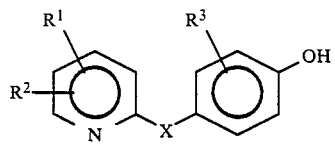

(II)

wherein $R^1$, $R^2$, $R^3$ and X have the same meanings as defined above, with a thiadiazole derivative represented by the formula (III):

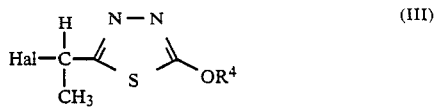

(III)

wherein $R^4$ represents the same meanings as defined above and Hal represents a halogen atom, in the presence of a base.

Examples of the base used in the reaction include inorganic base and organic base. As the inorganic base, alkali metal hydroxides such as sodium hydroxide and potassium hydroxide, and alkali metal carbonate such as sodium carbonate and potassium carbonate are mentioned. As the organic base, pyridine and triethylamine are mentioned. The reaction is usually carried out in a ketone such as acetone and methyl ethyl ketone, an aromatic hydrocarbon such as benzene and toluene, or a polar solvent such as tetrahydrofuran, acetonitrile, N,N-dimethylformamide and dimethylsulfoxide at a temperature within a range from 0° to 150° C., preferably, from 20° to 100° C.

The thiadiazole derivative according to the present invention represented by the formula (I) can also be produced by the following method. That is, it can be obtained through cyclization by intramolecular condensation of a hydrazine derivative represented by the formula (IV):

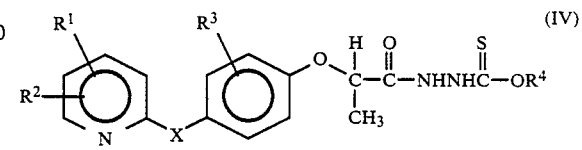

(IV)

wherein $R^1$, $R^2$, $R^3$, $R^4$ and X have the same meanings as defined above, In the presence of a dehydrating agent.

Examples of the dehydrating agent used herein include concentrated sulfuric acid, phosphorous pentoxide, phosphorous pentasulfide, polyphosphoric acid, acetic anhydride, methanesulfonic acid, etc. While the above reaction is usually carried out without solvent, it may be carried out depending on the case in an inert solvent such as aromatic hydrocarbons, for example, benzene, toluene and xylene, halogenated hydrocarbons, for example, methylene chloride, chloroform and 1,1,2,2-tetrachloroethane, or ethers, for example, ethyl ether, tetrahydrofuran and dioxane. The reaction temperature varies depending on the kind of the dehydrating agent and it is usually about from −10° to 200° C.

The hydrazine derivative represented by the formula (IV) can be produced according to such a method as disclosed in Japanese Patent Application Laying-Open (KOKAI) No. 57-200344 as follows.

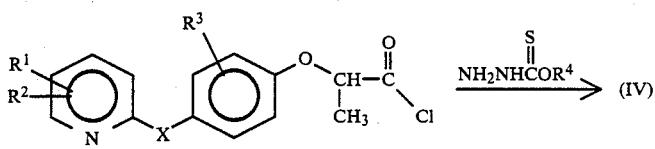

(IV)

The thiadiazole derivative according to the present invention represented by the formula (I) has a controlling activity against eggs and larvae of insects belonging to Coleoptera, Lepidoptera, Hemiptera, Orthoptera and Diptera as well as eggs and larvae of mites.

It is particularly effective to various plant-parasiting spider mites such as *Tetranychus urticae, Tetranychus cinnabarinus* and *Panonychus citri*, and exhibits excellent ovicidal activity and larvicidal activity.

In the case of using the thiadiazole derivative according to the present invention as an insecticide or a miticide, it may be used alone but is usually used by formulating together with adjuvants into various forms such as emulsifiable concentrate, dust, wettable powder and solution in accordance with the general method of preparing agricultural chemicals and used either without diluting or after diluting to a predetermined concentration using a diluent such as water.

The adjuvants can include solid carrier such as talc, kaolin, bentonite, diatomaceous earth, white carbon, clay and starch; liquid diluent such as water, toluene, xylene, chlorobenzene, cyclohexane, dimethylsulfoxide, dimethylformamide and alcohol; and surface active agent such as emulsifier, dispersant and spreader.

In addition, the thiadiazole derivative according to the present invention may also be mixed or combined with other agricultural chemicals, for example, other insecticide, miticide, fungicide and plant growth controlling agent.

The concentration of the thiadiazole derivative according to the present invention used varies depending on the plants to be treated, the method of application, the form of preparations, the applied amount, etc. and although it is not defined simply, it is usually from 1 to 1000 ppm and, preferably, from 20 to 500 ppm.

The present invention will further be explained specifically referring to examples and test examples, but it should be noted that the invention is not limited to the following examples.

EXAMPLE 1

2-Ethoxy-5-[1-[4-(2-pyridyloxy)phenoxy]ethyl]-1,3,4-thiadiazole

To a mixture of 4-(2-pyridyloxy)phenol (0.75 g), anhydrous potassium carbonate (0.67 g), potassium iodide (0.07 g), cupric oxide (0.02 g) and 7 ml of dimethyl formamide, was added 2-(1-bromoethyl)-5-ethoxy-1,3,4-thiadiazole (0.95 g) under stirring, and further stirred at 80° C. for one hour. After cooling and pouring water, the resulting solution was extracted with ethyl acetate, washed with water and then dried over anhydrous magnesium sulfate. Ethyl acetate was distilled off under a reduced pressure and the residue was purified on column chromatography to obtain 0.84 g of the compound (No. 1) described in Table 1.

EXAMPLE 2

2-Ethoxy-5-[1-[4-(5-chloro-2-pyridyloxy)phenoxy]ethyl]-1,3,4-thiadiazole

Concentrated sulfuric acid (10 ml) was cooled to −5° C. and ethyl 3-[2-[4-(5-chloro-2-pyridyloxy)phenoxy]-propionyl]thiocarbadinate (2.0 g) was added little by little under stirring. After stirring at the same temperature for 10 min, the resulting solution was poured into 100 g of ice-water, neutralized with an aqueous solution of sodium hydroxide and then extracted with ethyl acetate. The ethyl acetate layer was washed with water and dried over anhydrous sodium sulfate and then concentrated. The residue was purified on column chromatography to obtain 1.0 g of the compound (No. 2) described in Table 1.

Typical compounds of the present invention produced in the same manner as in Example 1 or 2 are shown in Table 1.

TABLE 1

| No. | Structure $R^1$ | $R^2$ | $R^3$ | $R^4$ | X | Physical property |
|---|---|---|---|---|---|---|
| 1 | H | H | H | $C_2H_5$ | O | $n_D^{25}$ 1.5790 |
| 2 | 5-Cl | " | " | " | " | mp 75–76° C. |
| 3 | 5-Br | " | " | " | " | mp 97–99° C. |
| 4 | 3-$CF_3$ | " | " | " | " | $n_D^{25}$ 1.5396 |
| 5 | 4-$CF_3$ | " | " | " | " | $n_D^{25}$ 1.5349 |
| 6 | 5-$CF_3$ | " | " | " | " | mp 69–70° C. |
| 7 | 6-$CF_3$ | " | " | " | " | $n_D^{25}$ 1.5341 |
| 8 | 5-$CO_2CH_3$ | " | " | " | " | mp 124–126° C. |
| 9 | 5-CN | H | H | $C_2H_5$ | O | mp 85–86° C. |
| 10 | 3-Cl | 5-Cl | " | " | " | $n_D^{25}$ 1.5913 |
| 11 | 3-Cl | 5-$CF_3$ | " | " | " | $n_D^{25}$ 1.5477 |
| 12 | 5-$CF_3$ | 6-Cl | " | " | O | mp 94–95° C. |
| 13 | 5-$CF_3$ | H | 2-F | " | " | $n_D^{24}$ 1.5322 |
| 14 | 5-$CF_3$ | " | H | $CH_3$ | " | mp 98–100° C. |
| 15 | 5-$CF_3$ | " | " | i-$C_3H_7$ | " | mp 83–84° C. |
| 16 | 5-Br | " | " | $C_2H_5$ | S | mp 79–81° C. |
| 17 | 5-$CF_3$ | " | " | " | S | mp 86–87.5° C. |
| 18 | 5-$CF_3$ | " | 2-Cl | " | O | $n_D^{24}$ 1.5483 |

Formulation examples of the compound according to the present invention are shown below, in which "parts" and "%" means "parts by weight" and "% by weight" respectively.

EXAMPLE 3

Wettable Powder

A wettable powder containing 40% of the effective ingredient was prepared by uniformly mixing and pulverizing 40 parts of the compound (No. 6) according to the present invention shown in Table 1, 20 parts of Carplex #80 (trade mark, manufactured by Shionogi Seiyaku Co.), 35 parts of N,N Kaolin Clay (trademark, manufactured by Tsuchiya Kaolin Co.), and 5 parts of Sorpol 8070, a higher alcohol sulfuric ester type surface active agent (trademark, manufactured by Toho Kagaku Co.).

EXAMPLE 4

Dust

A dust was prepared by uniformly mixing and pulverizing 2 parts of the compound (No. 12) according to the present invention shown in Table 1, 93 parts of NC Clay (trademark, manufactured by Goshima Kozan Co.) and 5 parts of Carplex #80 (trademark, manufactured by Shionogi Seiyaku Co.).

EXAMPLE 5

Emulsifiable Concentrate

An emulsifiable concentrate containing 30% of the effective ingredient was prepared by dissolving 30 parts of the compound according to the present invention (No. 13) shown in Table 1 into a mixed solvent comprising 30 parts of xylene and 25 parts of dimethylformamide and adding thereto 15 parts of Sorpol 3005X, a polyoxyethylene type surface active agent (trademark, manufactured by Toho Kagaku Co.).

EXAMPLE 6

Flowable Agent

A stable flowable composition containing 30% of the effective ingredient was prepared by thoroughly mixing and dispersing 30 parts of the compound (No. 14) according to the present invention shown in Table 1 into a previously prepared mixture of 8 parts of ethylene glycol, 5 parts of Sorpol AC 3032 (trademark, manufactured by Toho Kagaku Co.), 0.1 parts of xanthene gum and 56.9 parts of water and then pulverizing in a wet process the slurry-like mixture in a DYNO-MILL (trademark, manufactured by Shinmaru Enterprises Co.).

TEST EXAMPLE

Effect against *Tetranychus urticae*

Two female adult *Tetranychus urticae* were put to a leaf disc (2 cm diameter) of kidney beans leaf. They were allowed to oviposit for 20 hours after putting and then the female adults are removed. The formulation of each of the compounds according to the present invention obtained in accordance with the method in Example 3 was diluted with water to a predetermined concentration, into which the leaf disc after oviposition was immersed for 5 sec.

At tenth day after the treatment, the numbers of unhatched eggs and the dead larvae were examined, and the effect against eggs and larvae was determined by the following equation (Table 2).

Effect against ovum and larva (%) =

$$\frac{\text{Number of unhatched eggs} + \text{Number of dead larvae}}{\text{Number of treated eggs}} \times 100$$

TABLE 2

| Effect against *Tetranychus urticae* | | |
|---|---|---|
| Compound No. | Concentration (ppm) | Effect against eggs and larvae (%) |
| 1 | 500 | 80 |
| 2 | 500 | 100 |
| 3 | 200 | 100 |
|   | 500 | 100 |
| 4 | 200 | 100 |
|   | 500 | 90 |
| 5 | 500 | 100 |
|   | 200 | 95 |
| 6 | 500 | 100 |
|   | 200 | 100 |
| 7 | 500 | 95 |
| 8 | 500 | 90 |
| 9 | 500 | 100 |
|   | 200 | 90 |
| 10 | 500 | 85 |
| 11 | 500 | 90 |
| 12 | 500 | 100 |
|   | 200 | 100 |
| 13 | 500 | 100 |
|   | 200 | 100 |
| 14 | 500 | 100 |
|   | 200 | 100 |
| 15 | 500 | 100 |
|   | 200 | 100 |
| 16 | 500 | 80 |
| 17 | 500 | 90 |
| 18 | 500 | 100 |
|   | 200 | 100 |

What is claimed is:

1. A thiadiazole derivative represented by the formula (I):

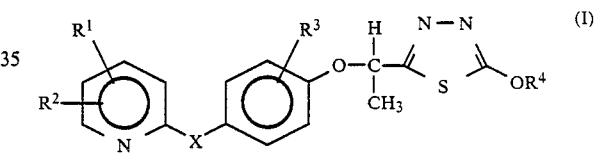

wherein $R^1$ and $R^2$ independently represent hydrogen atom, halogen atom, lower haloalkyl group, lower alkoxycarbonyl group or cyano group, $R^3$ represents hydrogen atom or halogen atom, $R^4$ represents lower alkyl group, X represents oxyen atom or sulfur atom.

2. The derivative according to claim 1, wherein said lower haloalkyl is a $C_1$–$C_4$ alkyl group which is substituted with 1 to 5 halogen atoms.

3. The derivative according to claim 1 wherein said lower alkoxycarbonyl group is an alkoxycarbonyl group having 2 to 5 carbon atoms.

4. The derivative according to claim 1, wherein said lower alkyl group is a $C_1$–$C_4$ alkyl group.

5. An insecticidal and miticidal composition comprising an insecticidally, and miticidally effective amount of a thiadiazole derivative, as the effective ingredient, represented by the formula (I):

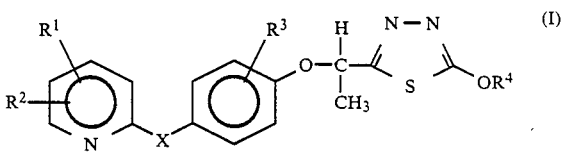

wherein $R^1$ and $R^2$ independently represent hydrogen atom, halogen atom, lower haloalkyl group, lower alkoxycarbonyl group or cyano group, $R^3$ represents hydrogen atom or halogen atom, $R^4$ represents lower alkyl group, X represents oxygen atom or sulfur atom, and
an insecticidally and miticidally acceptable adjuvant(s).

6. The insecticidal and miticidal composition according to claim 5, wherein said lower haloalkyl is a $C_1$–$C_4$ alkyl group which is substituted with 1 to 5 halogen atoms.

7. The insecticidal and miticidal composition according to claim 5, wherein said lower alkoxycarbonyl group is an alkoxycarbonyl group having 2 to 5 carbon atoms.

8. The insecticidal and miticidal composition according to claim 5, wherein said lower alkyl group is a $C_1$–$C_4$ alkyl group.

9. A method for controlling insects and mites which comprises applying an insecticidally and miticidally effective amount of a thiadiazole derivative represented by the following formula (I):

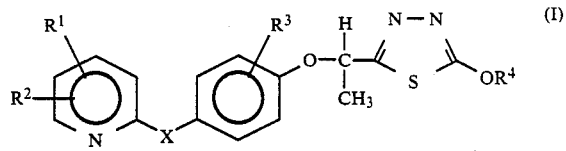

wherein $R^1$ and $R^2$ independently represent hydrogen atom, halogen atom, lower haloalkyl group, lower alkoxycarbonyl group or cyano group, $R^3$ represents hydrogen atom or halogen atom $R^4$ represents lower alkyl group, X represents oxygen atom or sulfur atom, to eggs or larvae of said insects of mites.

* * * * *